(12) United States Patent
Tavpash et al.

(10) Patent No.: US 11,369,512 B2
(45) Date of Patent: Jun. 28, 2022

(54) HEAT EXCHANGING PACK

(71) Applicants: Marharita-Sophia Tavpash, Bowling Green, OH (US); Andrew J. Szypka, Curtice, OH (US)

(72) Inventors: Marharita-Sophia Tavpash, Bowling Green, OH (US); Andrew J. Szypka, Curtice, OH (US)

( * ) Notice: Subject to any disclaimer, the term of this patent is extended or adjusted under 35 U.S.C. 154(b) by 1116 days.

(21) Appl. No.: 15/948,509

(22) Filed: Apr. 9, 2018

(65) Prior Publication Data

US 2018/0289532 A1 Oct. 11, 2018

Related U.S. Application Data

(60) Provisional application No. 62/483,573, filed on Apr. 10, 2017.

(51) Int. Cl.
*A61F 7/02* (2006.01)
*A61F 7/10* (2006.01)

(52) U.S. Cl.
CPC .............. *A61F 7/02* (2013.01); *A61F 7/103* (2013.01); *A61F 2007/0222* (2013.01); *A61F 2007/0225* (2013.01); *A61F 2007/0228* (2013.01); *A61F 2007/0231* (2013.01); *A61F 2007/105* (2013.01)

(58) Field of Classification Search
CPC .............. A61F 7/02; A61F 2007/0228; A61F 2007/105
See application file for complete search history.

(56) References Cited

U.S. PATENT DOCUMENTS

| 7,073,942 | B2 * | 7/2006 | Vazquez | A45C 7/0063 190/103 |
| 2004/0244414 | A1 * | 12/2004 | Trinh | F25D 3/08 62/530 |
| 2014/0364925 | A1 * | 12/2014 | Kilbey | A61F 7/10 607/96 |

* cited by examiner

*Primary Examiner* — Kaitlyn E Smith
(74) *Attorney, Agent, or Firm* — Shumaker, Loop & Kendrick, LLP; James D. Miller (57) ABSTRACT

A heat exchanging pack comprises a substance receiving portion, a first strap receiving portion disposed adjacent a first side of the substance receiving portion, a second strap receiving portion disposed adjacent a second side of the substance receiving portion, and a strap configured for releasably coupling the heat exchanging pack to a portion of a body. The strap includes a first portion extending through the first strap receiving portion, a second portion extending between the first strap receiving portion and the second strap receiving portion, a third portion extending through the second strap receiving portion, and a fourth portion extending out from the first strap receiving portion. The second portion and the fourth portion of the strap are configured to extend at least partially around a portion of a user in need of treatment to releasably couple the heat exchanging pack to the portion of the user.

18 Claims, 6 Drawing Sheets

HEAT EXCHANGING PACK

CROSS-REFERENCE TO RELATED APPLICATION

This application claims priority to U.S. Provisional Application Ser. No. 62/483,573 filed Apr. 10, 2017, the entire disclosure of which is hereby incorporated herein by reference.

FIELD OF THE INVENTION

The present invention relates to a reusable heat exchanging pack configured to be releasably coupled to a body of a user.

BACKGROUND OF THE INVENTION

Cold or hot packs are commonly used to treat a portion of a body of a user following a training session or injury. For example, it is common for a user to employ a cold or hot pack to various joints or muscles of the body following activities such as running, athletic competitions, or weight training in order to reduce pain or inflammation in the portion of the body of the user.

One drawback of the use of a cold or hot pack relates to a manner in which the pack must be placed in continual contact with the portion of the body of the user in order for adequate heat transfer to take place to provide a therapeutic effect. The attachment often requires the user to actively hold the pack against the portion of the body of the user or to reposition the body of the user in an uncomfortable position to maintain contact with the pack, each of which tend to make the process of using the pack unnecessarily uncomfortable and complex for the user.

Another problem associated with the use of cold or hot packs relates to the manner in which excessive air present within the pack reduces the heat transfer capabilities of a substance contained within the pack. This is especially true for a pack wherein the user places an independently formed cold or hot substance into a container of the pack prior to application of the pack to the desired portion of the body of the user. An air barrier present between the cold or hot substance located within the pack and an outer surface of the pack may inhibit the transfer of heat from the body of the user to the cold or hot substance. Additionally, a process of removing the excessive air from the pack usually includes the user trying to reseal an opening of the pack while simultaneously attempting to force the air out of the pack, wherein such a process is cumbersome, time consuming, and potentially may lead to leakage of the cold or hot substance from the pack.

Cold or hot packs are also typically manufactured for a single use before disposal of the pack. The single use of such packs leads to excessive waste and the need for the user to continually purchase additional packs, thereby costing the user additional money and time.

It would therefore be desirable to create a heat exchanging pack that is reusable, releasably coupled to a portion of a body of a user, and capable of conveniently and easily removing excessive air from within the heat exchanging pack for maximizing heat transfer.

SUMMARY OF THE INVENTION

In accordance with the present invention, a reusable heat exchanging pack capable of being releasably coupled to a portion of a user is disclosed.

In an embodiment of the current invention, a heat exchanging pack for treating a portion of a body is disclosed. The heat exchanging pack comprises a substance receiving portion configured to receive a cold or hot substance therein, a first strap receiving portion disposed adjacent a first side of the substance receiving portion, a second strap receiving portion disposed adjacent a second side of the substance receiving portion, and a strap configured for releasably coupling the heat exchanging pack to the portion of the body. The strap includes a first portion extending through the first strap receiving portion, a second portion extending between the first strap receiving portion and the second strap receiving portion, a third portion extending through the second strap receiving portion, and a fourth portion extending out from the first strap receiving portion.

A method of manufacturing a heat exchanging pack is also disclosed. The method comprises the steps of providing a bag, the bag including a first wall coupled to a second wall at a first side edge and an opposing second side edge of the bag; forming a first partitioning seam adjacent the first side edge, the first partitioning seam including a first portion of the first wall coupled to a first portion of the second wall, a first passageway formed between the first side edge and the first partitioning seam; and forming a second partitioning seam adjacent the second side edge, the second partitioning seam including a second portion of the first wall coupled to a second portion of the second wall, a second passageway formed between the second side edge and the second partitioning seam.

A method of using a heat exchanging pack is also disclosed. The method comprises the step of providing a heat exchanging pack comprising a substance receiving portion configured to receive a cold or hot substance therein, a first strap receiving portion disposed adjacent a first side of the substance receiving portion, a second strap receiving portion disposed adjacent a second side of the substance receiving portion, and a strap configured for releasably coupling the heat exchanging pack to the portion of the body. The strap includes a first portion extending through the first strap receiving portion, a second portion extending between the first strap receiving portion and the second strap receiving portion, a third portion extending through the second strap receiving portion, and a fourth portion extending out of the first strap receiving portion. The method further comprises the steps of placing a portion of a user between the substance receiving portion of the heat exchanging pack and the second portion of the strap and extending the fourth portion of the strap out of the first strap receiving portion to constrict the second portion of the strap around the portion of the user.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

DETAILED DESCRIPTION OF THE INVENTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Additionally, the dimensions provided in the drawings are merely for purposes of explaining the invention, and are not necessary or critical to operation of the invention unless otherwise stated herein. In respect of the methods disclosed, the steps presented are exemplary in nature, and thus, the order of the steps is not necessary or critical.

FIGS. 1-5 illustrate a heat exchanging pack 10 according to an embodiment of the invention. The heat exchanging pack 10 forms a container for selectively holding a cold or hot substance capable of exchanging heat energy with a portion of a body of a user such as a joint or muscle in need of therapy following a training session. The cold or hot substance may be any suitable cold or hot substance having the required characteristics for cooling or heating the desired portion of the body of the user. The cold or hot substance is produced independently of the heat exchanging pack 10 and may be user provided. The cold substance may be any frozen or cooled substance such as ice cubes while the hot substance may similarly be any heated substance such as a microwavable package of a soft gel refrigerate, as non-limiting examples. The cold or hot substance may be selected to include a suitable toxicity for the intended therapeutic use of the heat exchanging pack 10. The heat exchanging pack 10 is typically described hereinafter as receiving the cold substance in the form of ice cubes, but one skilled in the art should appreciate that any heat exchanging substance may be placed within the heat exchanging pack 10 and used to exchange heat energy through the heat exchanging pack 10 without necessarily departing from the scope of the present invention.

Figure 2:
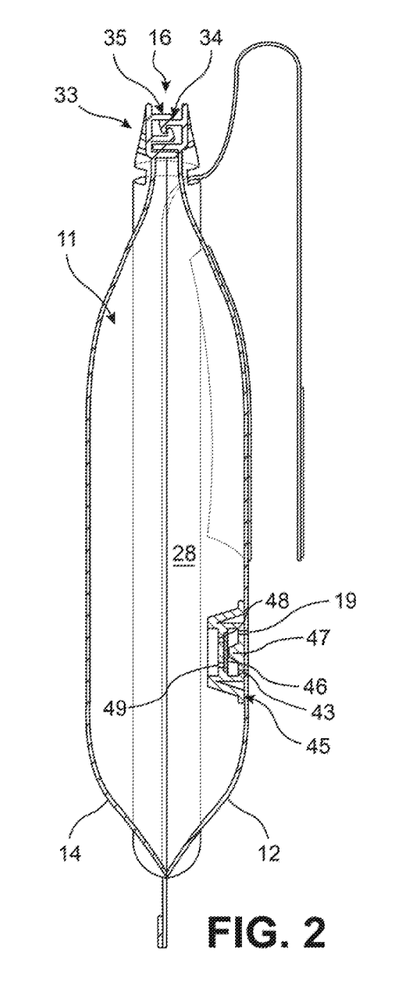
FIG. 2 is a cross-sectional elevational view of the heat exchanging pack of FIG. 1 showing a one-way valve of the heat exchanging pack prior to a flow of air out of the heat exchanging pack.

The heat exchanging pack 10 includes a first wall 12 and a second wall 14 (shown in FIG. 2). The first wall 12 and the second wall 14 may each be formed from a polymeric material having suitable flexibility for receiving a quantity of the cold or hot substance therein and suitable heat exchanging characteristics for exchanging heat energy between the cold or hot substance of the heat exchanging pack 10 and the portion of the body of the user in need of treatment. The first and second walls 12, 14 may be formed from a "film" of a thin polymeric material such as low-density polyethylene (LDPE), linear low-density polyethylene (LLDPE), high-density polyethylene (HDPE), or any other flexible material having desired heat exchanging characteristics, as non-limiting examples. The first and second walls 12, 14 may be formed from a clear plastic to allow for the user to visually inspect the condition of the cold or hot substance contained within the heat exchanging pack 10. The first and second walls 12, 14 may be formed from a thermoplastic polymer to allow for the walls 12, 14 to be joined to each other (or another component formed from a thermoplastic polymer) following a heating of the first and second walls 12, 14 such as during a heat sealing process. It should be understood that alternative polymeric materials having suitable characteristics may be used for forming the heat exchanging pack 10 without departing from the scope of the present invention.

Figure 1:
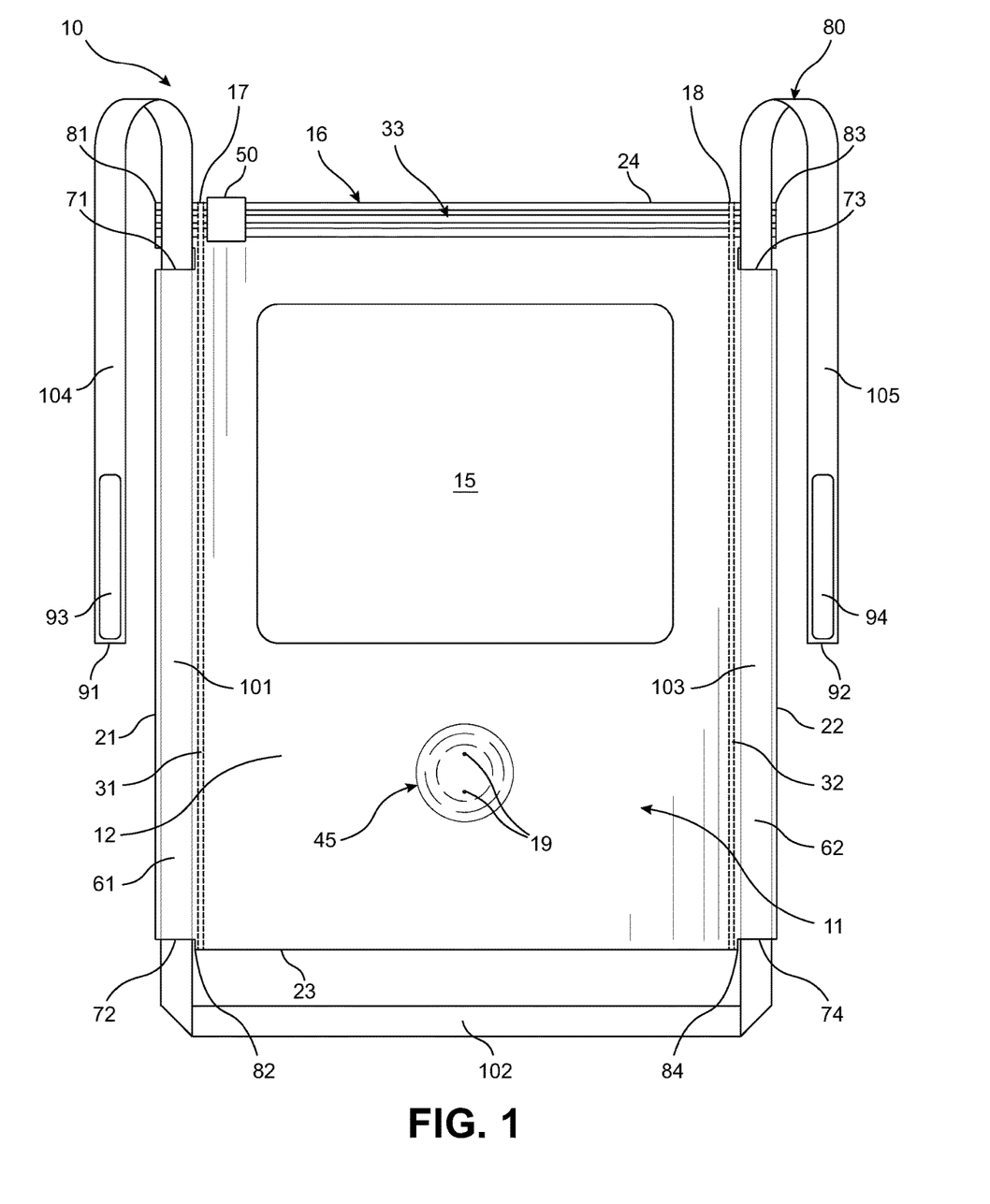
FIG. 1 is an elevational view of a heat exchanging pack according to an embodiment of the present invention.

The first wall 12 and the second wall 14 overlay each other and share a substantially similar or identical perimeter shape and size. In the embodiment shown in FIG. 1, the first wall 12 and the second wall 14 are each substantially rectangular in shape. However, alternative shapes may be used without departing from the scope of the present invention. A perimeter of the heat exchanging pack 10 includes a first side edge 21, an oppositely arranged second side edge 22, a first end edge 23, and an oppositely arranged second end edge 24. Generally speaking, the heat exchanging pack 10 may include any shape of the perimeter thereof wherein each of the first side surface 21 and the second side surface 22 extend away from the second end edge 24 in a direction transverse to the general direction of extension of the second end edge 24. For example, rather than being arranged in parallel as shown in FIG. 1, the first side edge 21 and the second side edge 22 may in some embodiments include an inward or outward taper as the side edges 21, 22 extend away from the second end edge 24, as desired.

The first wall 12 and the second wall 14 may be formed from a single common sheet of material folded about a portion of the common sheet forming the first end edge 23 thereof, thereby bringing a side edge of the first wall 12 into contact with a side edge of the second wall 14 to form the first side edge 21 while also bringing a side edge of the first wall 12 into contact with a side edge of the second wall 14 to form the second side edge 22. The first wall 12 and the second wall 14 may then be joined to each other at each of the first side edge 21 and the second side edge 22 by any suitable coupling method such as heat sealing. However, it is understood that other coupling methods may be employed such as stitching, an adhesive, ultrasonic sealing, or the like, so long as the first wall 12 and the second wall 14 are securely and sealingly coupled to each other. The folding of the common sheet of material may result in the first end edge 23 having a substantially rectilinear shape when joining the first side edge 21 to the opposing second side edge 22, as desired.

The heat exchanging pack 10 may alternatively be formed by two independent sheets of material joined together in place of the folding of the single sheet of material about the first end edge 23. In such a circumstance, the first wall 12 is joined to the second wall 14 at the first end edge 23 by a secure coupling method such as heat sealing in similar fashion to the formation of the first side edge 21 and the second side edge 22. The coupling of the two independent sheets of material may allow for the first end edge 23 of the heat exchanging pack 10 to have a desired shape or contour. For example, the first end edge 23 may be formed to include a substantially arcuate shape, as desired.

The heat exchanging pack 10 may further include a first partitioning seam 31 and a second partitioning seam 32. The first partitioning seam 31 is arranged adjacent and spaced from the first side edge 21 while the second partitioning seam 32 is arranged adjacent and spaced from the second side edge 22. The first partitioning seam 31 may extend substantially parallel to the first side edge 21 and the second partitioning seam 32 may extend substantially parallel to the second side edge 22. The first partitioning seam 31 may be spaced a first distance from the first side edge 21 and the second partitioning seam 32 may be spaced a second distance from the second side edge 22. The first distance and the second distance may each be about 1 inch or less, but alternative distances may be used without departing from the scope of the present invention. The first partitioning seam 31 and the second partitioning seam 32 extend from the second end edge 24 of the heat exchanging pack 10 to the first end edge 23 thereof. The first partitioning seam 31 and the second partitioning seam 32 each include a linearly extending portion of the first wall 12 securely coupled to a linearly extending portion of the second wall 14 by any suitable process, such as heat sealing, an adhesive, stitching, or the like, as desired.

A substance receiving portion 11 of the heat exchanging pack 10 is configured to receive the cold or hot substance therein. The substance receiving portion 11 is formed between the first wall 12 and the second wall 14 and is bounded by the first partitioning seam 31, the first end edge 23, the second partitioning seam 32, and a mouth 16 of the heat exchanging pack 10 formed adjacent the second end edge 24 thereof. The mouth 16 of the heat exchanging pack 10 is formed between the first wall 12 and the second wall 14 and provides access to an interior 28 (FIG. 2) of the substance receiving portion 11 when placing the cold or hot substance in the heat exchanging pack 10. The mouth 16 includes at least a portion of the first wall 12 selectively resealably coupled to at least a portion of the second wall 14 at or adjacent the second end edge 24 to either close or open the mouth 16 of the heat exchanging pack 10.

The mouth 16 may include a resealable mechanism 33 for releasably coupling a portion of the first wall 12 forming one side of the mouth 16 and a portion of the second wall 14 forming an opposing side of the mouth 16. The resealable mechanism 33 may include at least one first sealing structure 34 formed on the first wall 12 configured to cooperate with at least one second sealing structure 35 formed on the second wall 14. Each of the sealing structures 34, 35 extends longitudinally along a length of the mouth 16 in parallel to the second end edge 24 thereof. The sealing structures 34, 35 may include any suitable configuration of projections or indentations configured to engage each other to provide a hermetic seal between the sealing structures 34, 35 or otherwise seal against leakage of the heat exchanging substance disposed in the interior 28 of the heat exchanging pack 10.

The heat exchanging pack 10 is illustrated in FIG. 1 as having a slider mechanism 50 configured to join or release the sealing structures 34, 35 of the resealable mechanism 33 depending on a position of the slider mechanism 50 relative to a longitudinal direction of the mouth 16 of the heat exchanging pack 10. For example, FIG. 1 includes the slider mechanism 50 disposed adjacent a first end 17 of the mouth 16 representing a position of the slider mechanism 50 wherein the mouth 16 is closed and the sealing structures 34, 35 are engaged with each other along an entirety of the mouth 16. A movement of the slider mechanism 50 away from the first end 17 and towards an opposing second end 18 of the mouth 16 leads to a progressive disengagement of the sealing structures 34, 35 to progressively open the mouth 16. The heat exchanging pack 10 may include additional structural features such as slits, voids, openings, or stopping mechanisms disposed at or adjacent each end 17, 18 of the mouth 16 to restrict movement of the slider mechanism 50 between desired end positions for limiting a length of the resealable portion of the mouth 16. Examples of cooperating sealing structures used in conjunction with a slider mechanism for opening and closing a resealable package are disclosed in U.S. Pat. No. 5,964,532 to Phillips et al., U.S. Pat. No. 6,347,885 to Buchman, U.S. Pat. No. 6,364,530 to Buchman, and U.S. Pat. No. 7,029,178 to Gzybowski, each of which is incorporated herein by reference in its entirety. However, any form of resealable mechanism may be used for opening and closing the mouth 16 of the heat exchanging pack 10 without necessarily departing from the scope of the present invention. For example, it is understood that the sealing structures 34, 35 may be configured to operate in the absence of the slider mechanism 50, wherein the sealing structures 34, 35 are instead caused to engage each other via hand applied pressure and to disengage each other via a hand applied pulling of the walls 12, 14 from each other at the mouth 16. Further, suitable re-sealable tapes or adhesives could also be used, as desired.

The sealing structures 34, 35 may be formed by a suitable extrusion process during formation of the first and second walls 12, 14 or may be formed by any other suitable manufacturing process. For example, the sealing structures 34, 35 may be formed at opposing lateral ends of an extruded sheet of material that is subsequently folded about a central portion thereof (forming the first end edge 23) when a single sheet of material is used to form both the first wall 12 and the second wall 14. Alternatively, a first sheet forming the first wall 12 may include one set of the sealing structures 34, 35 along an end thereof while a second sheet forming the second wall 14 may also include a complimentary set of the sealing structures 34, 35 along an end thereof, wherein the two sheets are joined to bring the sealing structures 34, 35 in alignment with each other. As shown in FIG. 1, the heat sealing process used to form the first partitioning seam 31 and the second partitioning seam 32 may be applied to the heat exchanging pack 10 after the sealing structures 34, 35 are already engaged with each other, thereby effectively establishing end points for the mouth 16 due to the thermoplastic joining of the first wall 12 to the second wall 14 at the positions where the partitioning seams 31, 32 intersect the interlocked sealing structures 34, 35.

The interior 28 of the substance receiving portion 11 of the heat exchanging pack 10 is configured to be hermetically sealed at each of the first partitioning seam 31, the first end edge 23, the second partitioning seam 32, and the mouth 16 thereof when the mouth 16 is in a closed position. As mentioned hereinabove, the first partitioning seam 31 and the second partitioning seam 32 may be formed by a heat sealing process suitable for at least partially melting the engaging portions of each of the first wall 12 and the second wall 14 prior to a subsequent cooling of the engaging portions of the first wall 12 and the second wall 14 to form the hermetic seal along a length of each of the first partitioning seam 31 and the second partitioning seam 32. The first end edge 23 may be a folded portion of a common sheet of material forming both the first wall 12 and the second wall 14 or the first end edge 23 may be formed by a heat sealing process joining the first wall 12 to the second wall 14 to form the hermetic seal. The hermetic sealing of the mouth 16 is dependent on the engagement of the first sealing structures 34 of the first wall 12 with the second sealing structures 35 of the second wall 14.

The heat exchanging pack 10 further includes a first passageway 61 and a second passageway 62 configured to receive a strap 80 or other elongate material or fastening material suitable for securing the heat exchanging pack 10 to the body of the user therein. The first passageway 61 is formed by a portion of the heat exchanging pack 10 disposed between the first partitioning seam 31 and the first side edge 21 while the second passageway 62 is formed by a portion of the heat exchanging pack 10 disposed between the second partitioning seam 32 and the second side edge 22. The first passageway 61 and the second passageway 62 each include a portion of the first wall 12 separated from a portion of the second wall 14 to form a hollow opening for reception of the strap 80. A first opening 71 is formed at or adjacent a first end 81 of the first passageway 61 and a second opening 72 is formed at or adjacent a second end 82 thereof. The first and second openings 71, 72 of the first passageway 61 may have any suitable shape and size suitable for allowing the strap 80 to extend therethrough. A first opening 73 is formed at or adjacent a first end 83 of the second passageway 62 and a second opening 74 is formed at or adjacent a second end 84 thereof. The first and second openings 73, 74 of the second passageway 62 may similarly have any suitable shape and size suitable for allowing the strap 80 to extend therethrough. In the embodiment shown in FIG. 1, the first openings 71, 73 are formed at a position adjacent and under the sealing structures 34, 35 of the resealable mechanism 33 while the second openings 72, 74 are shown as formed directly at the second end 82, 84 of each of the passageways 61, 62. The openings 71, 72, 73, 74 may be formed by any suitable cutting or punching operation performed with respect to the first and second walls 12, 14 forming the heat exchanging pack 10, as desired.

The heat exchanging pack 10 may alternatively include any suitable strap receiving structure for receiving the strap 80 along each of the two opposing sides of the substance receiving portion 11. For example, the heat exchanging pack 10 may include a plurality of spaced apart looped structures projecting from each side of the substance receiving portion 11 in place of the longitudinally extending passageways 61, 62.

The strap 80 extends longitudinally from a first end 91 to a second end 92 thereof. As used herein, the term "strap" may refer to any flexible component having a much greater length in comparison to any dimension of the component arranged perpendicular to the length direction thereof. The strap 80 may have any suitable cross-sectional shape, including elliptical, circular, or rectangular, as desired. The strap 80 may be formed from any suitable material having a suitable tensile strength and flexibility. In the embodiment shown in FIG. 1, the strap 80 includes a rectangular cross-sectional shape and is formed from a polymeric material such as LDPE, LLDPE, or HDPE, as non-limiting examples. The strap 80 may be substantially similar in form to a tie-string of a disposable garbage bag, for example. The string may alternatively be formed from string, yarn, rope, nylon, or the like, as desired.

As best shown in FIG. 1, the strap 80 includes a first portion 101 disposed in the first passageway 61, a second portion 102 extending between the second opening 72 of the first passageway 61 and the second opening 74 of the second passageway 62, and a third portion 103 disposed in the second passageway 62. The strap 80 further includes a fourth portion 104 extending out from the first opening 71 of the first passageway 61 and a fifth portion 105 extending out from the first opening 73 of the second passageway 62. The fourth portion 104 terminates at the first end 91 of the strap while the fifth portion terminates at the second end 92 of the strap 80. The strap 80 is configured to be slidable within each of the first passageway 61 and the second passageway 62 in a manner wherein a pulling of one of the fourth portion 104 or the fifth portion 105 of the strap 80 results in a change in which portions of the strap 80 constitute each of the stated portions 101, 102, 103, 104, 105 thereof. The strap 80 may be provided with an adjustable feature (not shown) for altering a length of the strap 80, as desired. Alternatively, the heat exchanging pack 10 may be provided with straps 80 of different lengths to accommodate different portions of the user of the body. For example, a different strap length may be desired for coupling the heat exchanging pack 10 to the wrist of the user as opposed to the thigh of the user due to the substantial increase in outer diameter between the wrist and the thigh. The strap 80 may also be provided with a length great enough to extend around the portion of the user at least once for larger diameter portions of the user while extending around smaller diameter portions multiple times, thereby allowing for the heat exchanging pack 10 to be adjusted for use with any portion of the body of the user.

The first end 91 of the strap 80 may include a first coupling device 93 and the second end 92 of the strap may include a second coupling device 94. In the embodiment illustrated in FIGS. 1-5, each of the first and second coupling devices 93, 94 includes a surface having one of a hook pattern or a loop pattern of a hook-and-loop coupling system. An exterior surface of the first wall 12 includes a coupling surface 15 disposed thereon having the other of the hook pattern or the loop pattern for cooperating with each of the coupling devices 93, 94. The coupling devices 93, 94 and the coupling surface 15 may be formed from complimentary hook-and-loop components found in commercially available hook-and-loop tapes, wherein a hook pattern tape and a loop pattern tape are distributed between the cooperating surfaces to allow the coupling devices 93, 94 to be releasably coupled to the coupling surface 15 of the first wall 12.

Alternatively, in one exemplary embodiment of the heat exchanging pack 10, the coupling surface 15 is formed by a sheet of non-woven spunbond polypropylene coupled to the exterior surface of the first wall 12 for forming the loop pattern while each of the coupling devices 93, 94 includes a sheet of a hook tape having the hook pattern suitable for engaging and grasping the loop pattern of the sheet of the spunbond polypropylene. The sheet of the spunbond polypropylene may be coupled to the first wall 12 by use of a cold adhesive, but it is understood that any suitable coupling method may be used. The spunbond polypropylene may be provided at a density between 15-22 $g/m^2$ to ensure that the hook pattern of each of the coupling devices 93, 94 is able to sufficiently grasp the loop pattern formed by the spunbond polypropylene.

The coupling surface 15 is shown as being substantially rectangular, but it is understood that the coupling surface 15 may have any suitable shape and size while remaining within the scope of the present invention. In some embodiments, the coupling surface 15 may only be present at select locations along a length of the heat exchanging pack 10 while in other embodiments the coupling surface 15 may cover a majority of the exterior surface of the first wall 12 to allow for the coupling devices 93, 94 to be coupled to any desired portion of the first wall 12.

The heat exchanging pack 10 further includes a one-way valve 45 configured for venting air out of the interior 28 of the heat exchanging pack 10 when the mouth 16 of the heat exchanging pack 10 is hermetically sealed via use of the resealable mechanism 33. The one-way valve 45 may be any form of one-way valve 45 suitable for operating at the pressures normally experienced within the heat exchanging pack 10. The one-way valve 45 may preferably be formed from a low-cost thermoplastic material, such as polyethylene or polyethylene terephthalate, as non-limiting examples.

Figure 3:
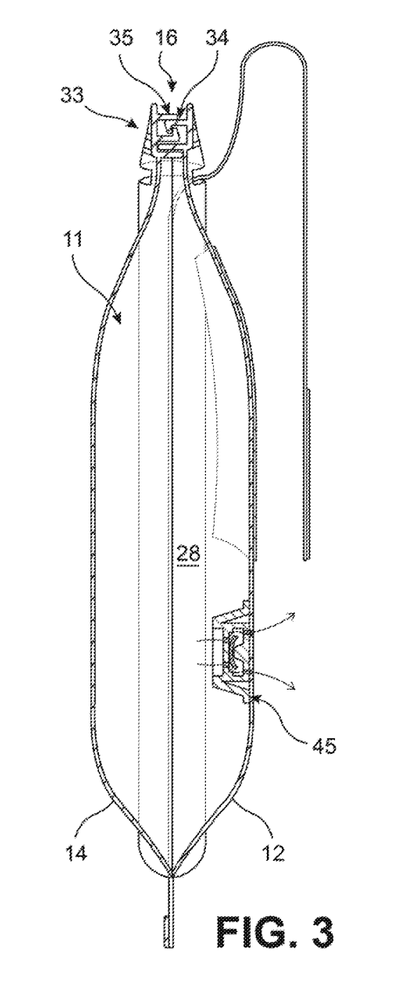
FIG. 3 is a cross-sectional elevational view of the heat exchanging pack showing the one-way valve of FIG. 2 during a flow of air out of the heat exchanging pack.

The one-way valve 45 generally includes a flexible member 46 configured to normally close the one-way valve 45 (FIG. 2) and to open the one-way valve 45 when a pressure within the interior 28 of the substance receiving portion 11 exceeds a pressure of the ambient environment by a predetermined pressure value (FIG. 3). The one-way valve 45 is illustrated in FIGS. 2 and 3 as having a pivot member 47 about which a radially outermost portion of the flexible member 46 flexes away from a sealing surface 48 of the one-way valve 45 to provide fluid communication between the interior of the one-way valve 45 and the interior 28 of the heat exchanging pack 10 via one or more holes 49 formed in the sealing surface 48. The air disposed within the interior of the one-way valve 45 is then able to flow out of the one-way valve 45 via one or more openings 43 formed in the one-way valve 45 in alignment with apertures 19 formed in the first wall 12. However, it should be appreciated that the structure of the one-way valve 45 shown in FIGS. 2 and 3 is not limiting, and that any suitable structural relationship suitable for providing a one-way flow of air out of the heat exchanging pack 10 may be used without departing from the scope of the present invention. The one-way valve 45 may be a degassing valve such as those normally used for venting excessive carbon dioxide accumulated in packaging for products such as coffee beans and the like, as one non-limiting example. It is understood other types of valves can be used which facilitate removal of excess air from the interior 28 of the heat exchanging pack 10. Further, simple hand pumps could also be used to evacuate the excess air.

The one-way valve 45 may be securely coupled to the heat exchanging pack 10 using any desired structure and method. For example, the one-way valve 45 is illustrated in FIGS. 2 and 3 as being entirely disposed within the interior 28 of the substance receiving portion 11 and in abutment within an interior surface of the first wall 12. The one-way valve 45 may be adhered to the first wall 12 by a heat sealing process applied to an exterior surface of the first wall 12 when the one-way valve 45 is in abutment with the interior surface of the first wall 12. The one-way valve 45 may be coupled to the first wall 12 prior to the formation of the interior 28 of the substance receiving portion 11 via the joining of the first wall 12 to the second wall 14 at any of the side edges 21, 22, the partitioning seams 31, 32, the mouth 16, and optionally the first end edge 23 (if two independent sheets of material are used to form the heat exchanging pack 10 as opposed to a folded sheet of material). The heat sealing process may further include one or more pins extending from the heating element performing the heat sealing process, wherein the pin or pins are used to punch out each of the apertures 19 formed through the first wall 12 for providing fluid communication between the ambient environment and the interior of the one-way valve 45. However, the one-way valve 45 may alternatively be coupled to the interior surface of the first wall 12 by any method, including adhesives and the like. The apertures 19 may also be formed in an independent manufacturing step wherein the first wall 12 is punctured or cut using any known method, as desired.

Alternative structural relationships may be present between the one-way valve 45 and the first wall 12 of the heat exchanging pack 10. For example, the first wall 12 may include an opening configured to receive a peripheral portion of the one-way valve 45 therein in a manner wherein one face of the one-way valve 45 faces outwardly toward the ambient environment while an oppositely arranged face of the one-way valve 45 faces towards the interior 28 of the substance receiving portion 11 of the heat exchanging pack 10. The one-way valve 45 may then be coupled to the first wall 12 by any suitable method, such as a heat sealing process applied adjacent the periphery of the one-way valve 45.

Figure 4:
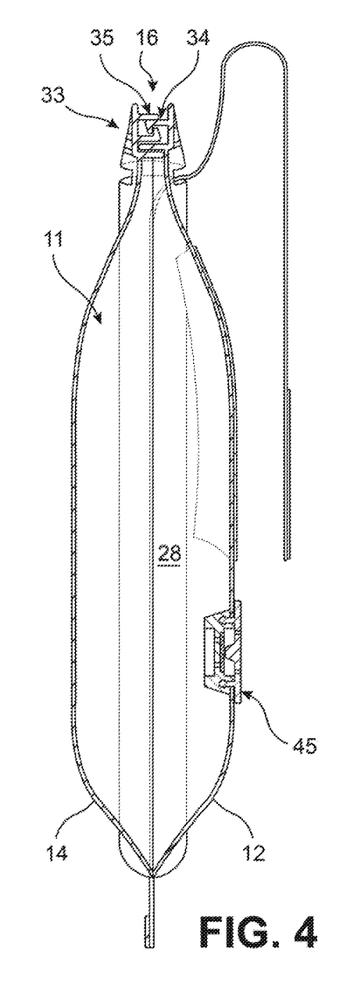
FIG. 4 is a cross-sectional elevational view of the heat exchanging pack showing a two-part one-way valve.
Figure 5:
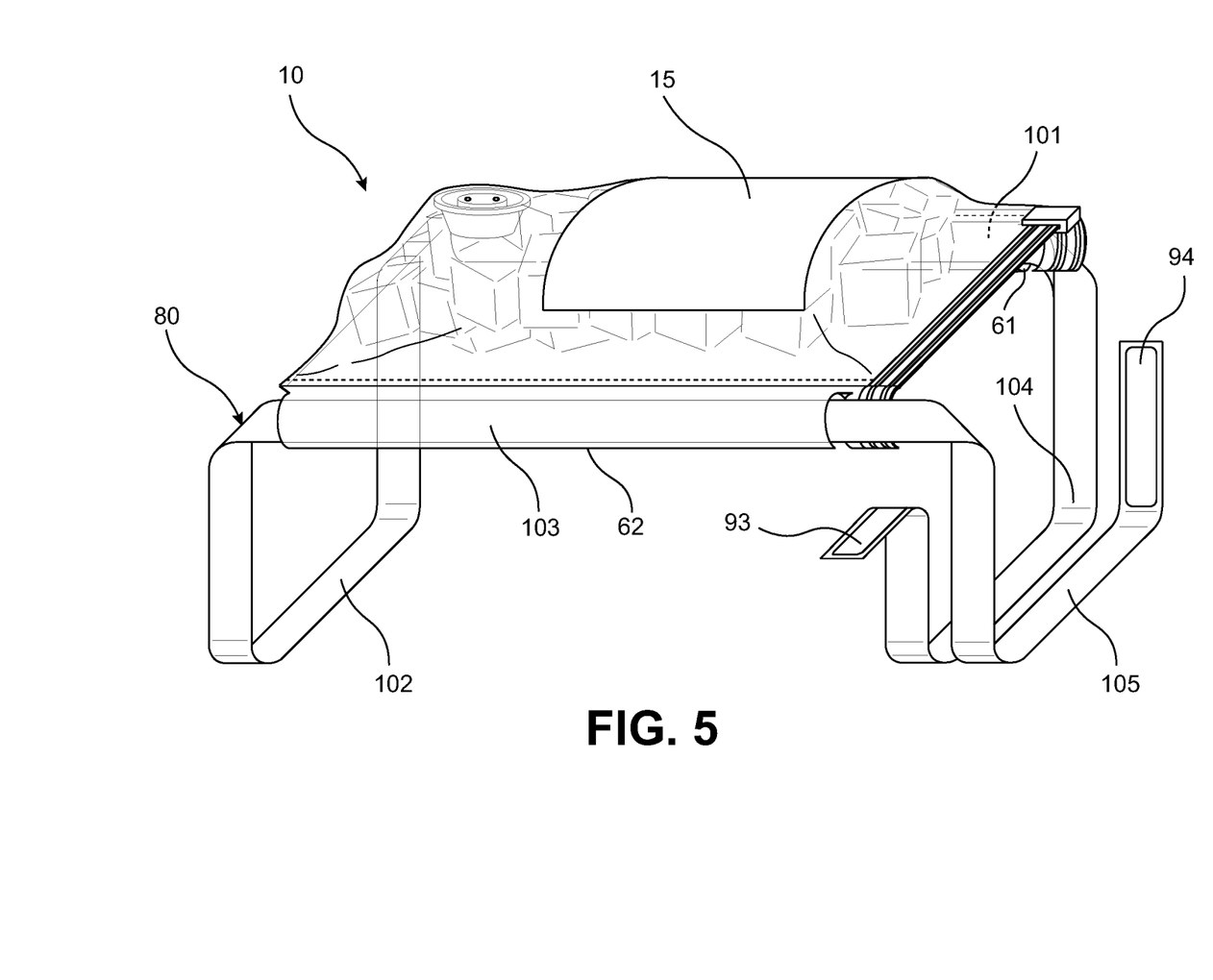
FIG. 5 is a perspective view of the heat exchanging pack showing a strap thereof forming loops for receiving a portion of the user therein.

As shown in FIG. 4, the one-way valve 45 may alternatively be formed from a pair of complimentary components that are joined to each other with at least a portion of the first wall 12 disposed therebetween. The cooperating components may be configured to snap-fit to each other while simultaneously penetrating the portion of the first wall 12 surrounded by the resulting one-way valve 45 for providing the selective fluid communication between the ambient environment and the interior 28 of the substance receiving portion 11. The assembly of the cooperating components may provide a hermetic seal about the periphery of the resulting one-way valve 45 based on cooperating structures formed in each of the components. One skilled in the art should appreciate that a variety of different methods and configurations may be used for coupling the one-way valve 45 to the first wall 12 in a manner allowing for selective removal of excess air from within the interior 28 of the substance receiving portion 11.

The heat exchanging pack 10 may be produced by modifying a bag already having the first wall 12 and the second wall 14 coupled around at least a periphery of the bag, wherein the first wall 12 and the second wall 14 may be portions of a single sheet of material separated by a fold or two independent sheets of material coupled to each other. The bag may also be provided to include the resealable mechanism 33 and the slider mechanism 50. The process of producing the heat exchanging pack 10 may include the formation of the first and second partitioning seams 31, 32 in the bag to form the first and second passageways 61, 62, the punching or cutting of the openings 71, 72, 73, 74 from each of the passageways 61, 62, and then the insertion of the strap 80 into and out of the passageways 61, 62 as described hereinabove. The process of producing the heat exchanging pack 10 may further include the coupling of each of the one-way valve 45 and the coupling surface 15 to the bag by the methods disclosed hereinabove.

In use, the resealable mechanism 33 is adjusted to open the mouth 16 of the heat exchanging pack 10, wherein the opening of the mouth 16 may include a repositioning of the slider mechanism 50 to disengage the sealing structures 34, 35 forming the sealing mechanism 33 of the mouth 16. Once the mouth 16 is opened, a quantity of a cold or hot substance such as a plurality of ice cubes is disposed within the interior 28 of the substance receiving portion 11 until the interior 28 is sufficiently filled with the cold or hot substance according to the desires of the user. The mouth 16 is then closed and resealed via use of the resealable mechanism 33 to hermetically seal the interior 28 of the substance receiving portion 11 from the ambient environment. Typically, a quantity of undesired excess air is disposed within the interior 28 of the substance receiving portion 11 following the closing and sealing of the mouth 16. The excess air is removed from the substance receiving portion 11 by a squeezing or compressing of the substance receiving portion 11 to cause the interior 28 thereof to increase to a pressure greater than the pressure of the ambient environment until the one-way valve 45 is caused to outlet a quantity of the excess air out of the substance receiving portion 11. The removal of the excess air causes the first and second walls 12, 14 to closely conform to a shape of the cold or hot substance disposed in the substance receiving portion 11, thereby improving heat exchange between the cold or hot substance and each of the walls 12, 14 forming the heat exchanging pack 10.

The heat exchanging pack 10 is then releasably coupled to a portion of a user's body by use of the strap 80. The heat exchanging pack 10 may be coupled to any desired portion of the user's body capable of receiving the strap 80 therearound. As explained hereinabove, the strap 80 includes fourth and fifth portions 104, 105 extending adjacent the mouth 16 of the heat exchanging pack 10, wherein each of the fourth and fifth portions 104, 105 includes one of the coupling devices 93, 94. As best shown with reference to FIG. 5, the second portion 102 of the strap 80 extending between the first and second passages 61, 62 cooperates with an end of the substance receiving portion 11 to form a first loop or opening configured to receive the portion of the user therein. The first coupling device 93 of the fourth portion 104 of the strap 80 is caused to extend around the portion of the user before being releasably coupled to the coupling surface 15 formed on the first wall 12 to form a second loop or opening receiving the portion of the user therein. The second coupling device 94 is similarly extended around the portion of the user before being releasably coupled to the coupling surface 15 for forming a third loop or opening also receiving the portion of the user therein.

It should be understood that the strap 80 may be selected to be any desired length suitable for extending around the desired portion of the user any number of times before the coupling devices 93, 94 are coupled to the coupling surface 15. For example, the strap 80 may have a length suitable wherein the fourth and fifth portions 104, 105 extend around the portion of the user once while also tightening the first loop formed by the second portion 102 adequately for securing the heat exchanging pack 10 to the user. Alternatively, the strap 80 may have a suitable length for extending the fourth and fifth portions 104, 105 around the portion of the user twice each so as to form two additional loops around the portion of the user. The use of the lengthier strap 80 may aid in securing the heat exchanging pack 10 to the user by allowing the loops to be formed at multiple different positions with respect to the longitudinal direction of the heat exchanging pack 10, as desired.

During the extending of one or both of the coupling devices 93, 94 about the portion of the user the strap 80 is extended in a manner causing the first loop formed by the second portion 102 of the strap 80 to constrict about the portion of the user to tighten the heat exchanging pack 10 thereto. The coupling devices 93, 94 may be pulled about the portion of the user to a desired position on the coupling surface 15 that also causes the second and third loops to constrict around the portion of the user.

The presence of the cold or hot substance within the substance receiving portion 11 of the heat exchanging pack 10 beneficially allows for the tightening of the different loops without causing the strap 80 to excessively constrict a longitudinal dimension of either of the passageways 61, 62, which aids in ensuring that the heat exchanging pack 10 maintains a desired general shape during the process of coupling the heat exchanging pack 10 to the user. The lack of substantial longitudinal constriction of the passageways 61, 62 also allows for the surfaces of the passageways 61, 62 defining each of the openings 71, 72, 73, 74 to act as pivot points about which the strap 80 turns transversely away from the longitudinal direction of the passageways 61, 62 during the tightening of the heat exchanging pack 10 to the user. Furthermore, the spacing of each of the partitioning seams 31, 32 from each respective side edge 21, 22 of the heat exchanging pack 10 allows for the passageways 61, 62 to pivot about the partitioning seams 31, 32. The pivoting of the passageways 61, 62 about the partitioning seams 31, 32 allows for the passageways 61, 62 to extend partially around the portion of the user on either side thereof for securely affixing the heat exchanging pack 10 to the desired position on the user.

Figure 6:
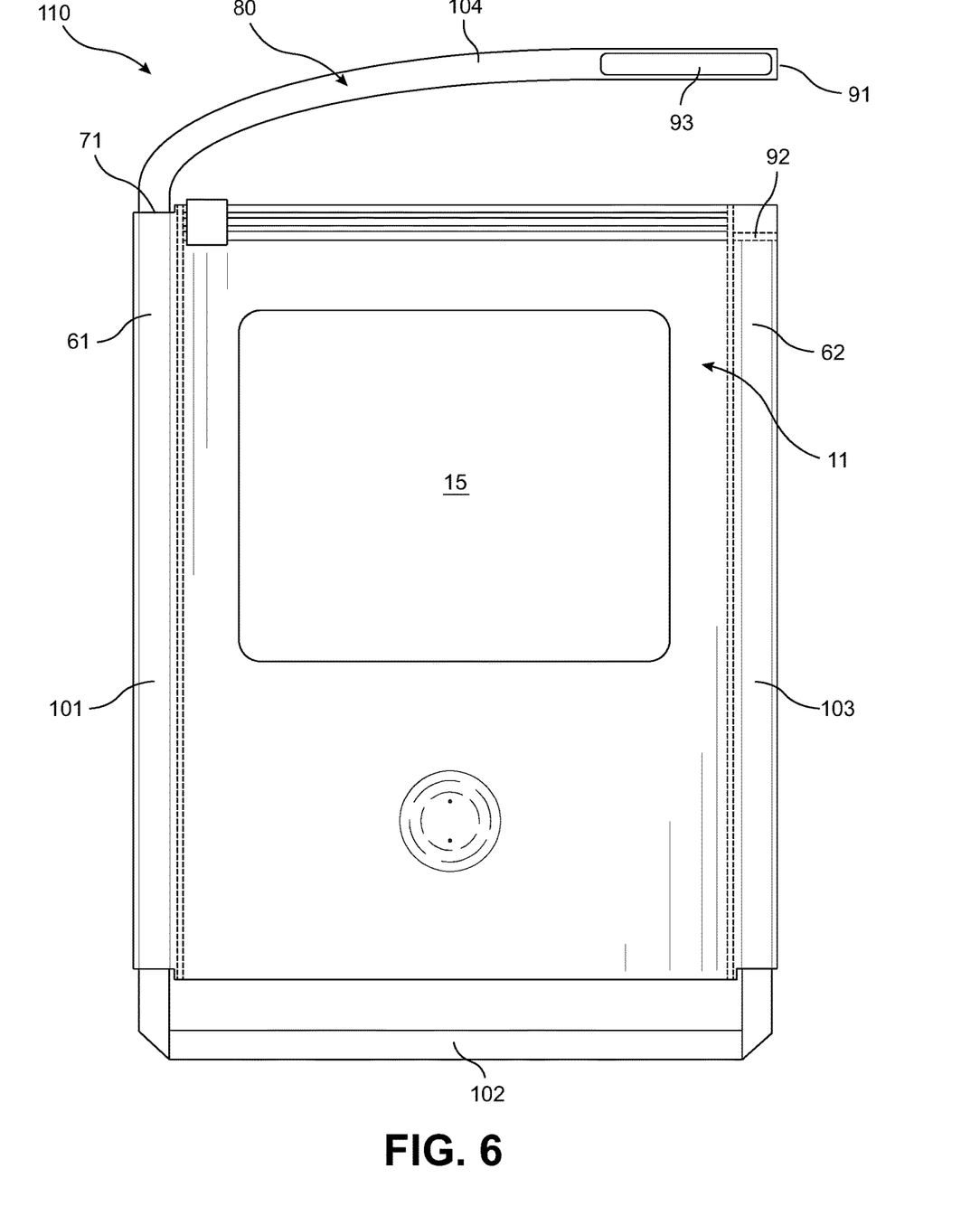
FIG. 6 is an elevational view of a heat exchanging pack having a strap according to another embodiment of the present invention.
Figure 7:
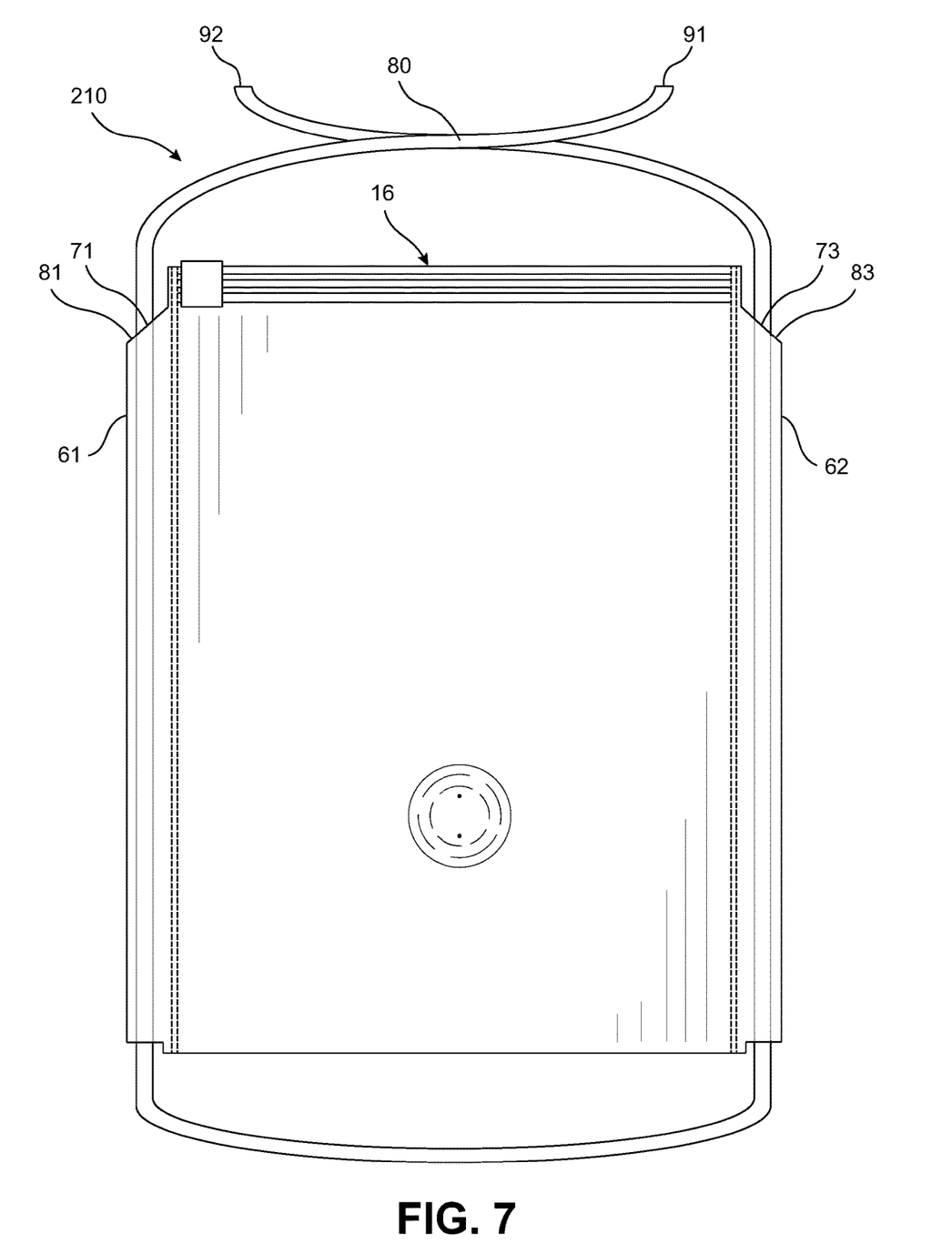
FIG. 7 is an elevational view of a heat exchanging pack having passageways and a strap according to another embodiment of the present invention.
Figure 8:
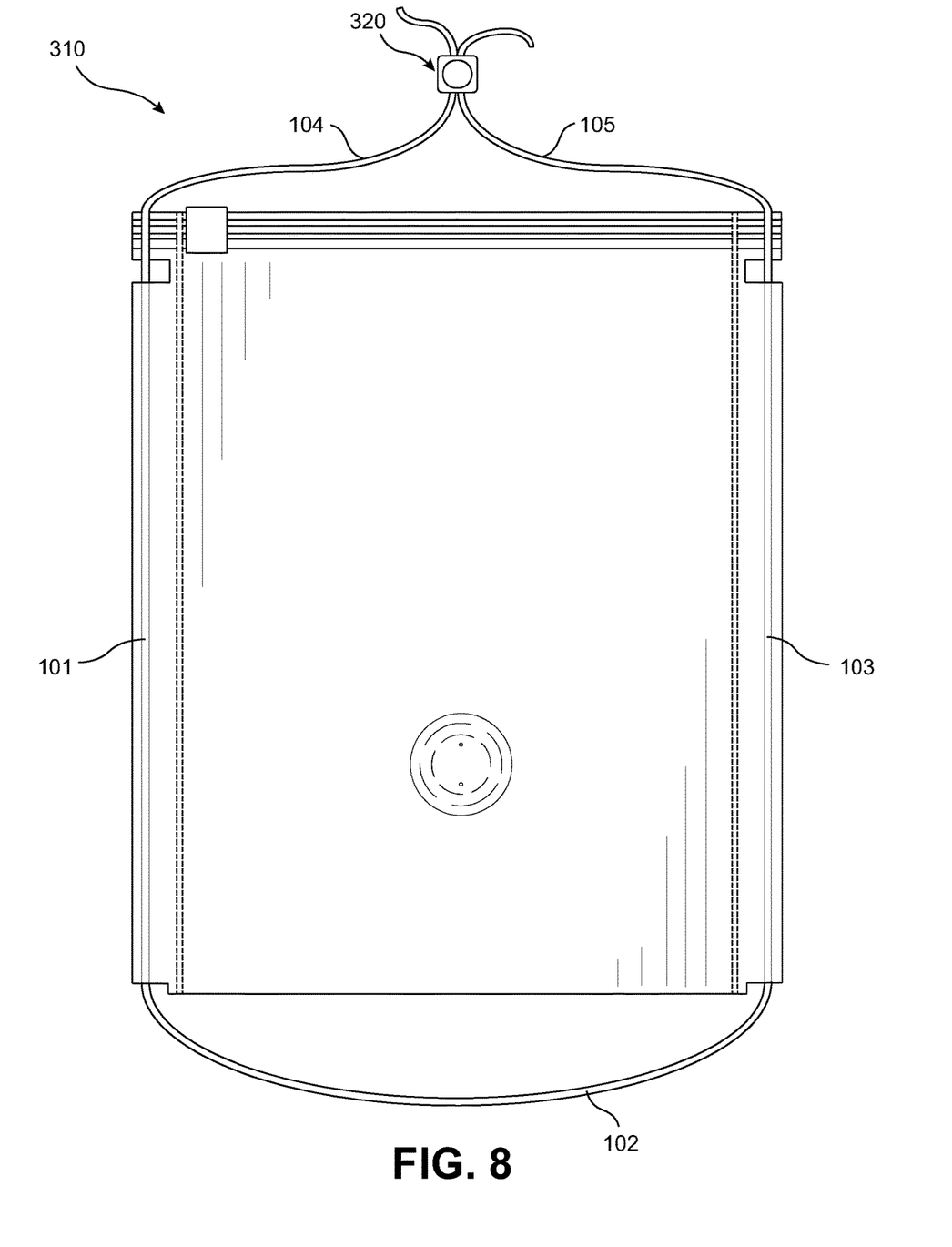
FIG. 8 is an elevational view of a heat exchanging pack having a strap with a draw-string type coupling device according to another embodiment of the present invention.

FIGS. 6-8 illustrate various modifications to the heat exchanging pack 10 illustrated in FIGS. 1-5 while remaining within the scope of the present invention. A heat exchanging pack 110 shown in FIG. 6 includes a strap 80 devoid of the fifth portion 105 extending out of the second passageway 62. Instead, the second end 92 of the strap 80 is securely coupled to the substance receiving portion 11 at or adjacent the second end 83 of the second passageway 62 to affix a position of the second end 92 of the strap 80. The second end 92 of the strap 80 may be positioned between the first and second walls 12, 14 prior to a coupling of the first and second walls 12, 14 to each other, such as by heat sealing, stitching, adhesives, or the like, as desired. The heat exchanging pack 110 operates via extension of the fourth portion 104 of the strap 80 out of the first opening 71 of the first passageway 61 and around the portion of the user, which in turn tightens both the first loop formed by the second portion 102 of the strap 80 and the second loop formed by the fourth portion 104 of the strap 80 before the first coupling device 93 is coupled to the coupling surface 15. The heat exchanging pack 110 advantageously simplifies the securing of the heat exchanging pack 10 to the portion of the user by requiring the pulling and securing of only the fourth portion 104 of the strap 80. The heat exchanging pack 110 may include a strap 80 of any desired length, including a strap 80 long enough to ensure that the strap 80 is wrapped around the portion of the user multiple times, as desired.

A heat exchanging pack 210 illustrated in FIG. 7 includes two modifications from the heat exchanging pack 10 of FIGS. 1-5. First, the strap 80 is devoid of any form of coupling device at either end thereof. Instead, the first end 91 and the second end 92 of the strap 80 are configured to be hand-tied to each other to form at least one loop adjacent the mouth 16 of the heat exchanging pack 210 for securing the heat exchanging pack 210 to the portion of the user. The heat exchanging pack 210 also shows a modification wherein the first ends 81, 83 of the passageways 61, 62 are removed to an extent that the sealing structures formed to either side of the mouth 16 of the heat exchanging pack 210 are removed to form the first openings 71, 73 of the passageways 61, 62. The removal of the first ends 81, 83 of the passageways 61, 62 may be accomplished by any form of cutting or punching operation carried out on the first and second walls 12, 14 prior to placement of the strap 80 in either of the passageways 61, 62.

FIG. 8 illustrates a heat exchanging pack 310 that is substantially similar to the heat exchanging pack 10 except for the replacement of the coupling devices 93, 94 with a single coupling device 320. The coupling device 320 may be a spring-loaded drawstring toggle as is known in the art. The drawstring toggle operates wherein compression of the toggle opposes the force of the spring included therein to align two otherwise offset openings with each other in a manner allowing the fourth and fifth portions 104, 105 of the strap 80 to be extended or retracted through the toggle. A release of the compression applied to the toggle causes the openings to once again be offset from each other in a manner causing the fourth and fifth portions 104, 105 of the strap 80 to be compressed between two cooperating portions of the toggle. The coupling device 320 may accordingly be used to tighten both the first loop formed by the second portion 102 of the strap 80 and a second loop formed by the cooperation of the fourth and fifth portions 104, 105 as a greater length of the fourth and fifth portions 104, 105 is drawn through the coupling device 320. Although a drawstring toggle structure is shown and described, one skilled in the art should appreciate that any form of coupling device 320 suitable for affixing a longitudinal position of either or both of the fourth portion 104 and the fifth portion 105 of the strap 80 relative to the coupling device 320 may be used without departing from the scope of the present invention. For example, the coupling device 320 may be any type of clip, clamp, fastener, or the like, as desired. The use of the coupling device 320 may result in the strap 80 being formed from a string, rope, or chord-like material having a substantially circular or elliptical cross-sectional shape for better feeding the strap 80 through the coupling device 320 in comparison to an extruded polymeric material having a substantially rectangular cross-sectional shape, as desired.

It should be appreciated that each of the alternative structural features discussed with reference to the heat exchanging packs 110, 210, 310 disclosed in FIGS. 6-8 may be used in conjunction with any other structural features disclosed herein to form a heat exchanging pack having the desired characteristics for releasably coupling the heat exchanging pack to the portion of the user while remaining within the scope of the present invention. For example, the alternative form of the openings 71, 73 shown and described with reference to FIG. 7 may be used in conjunction with any of the heat exchanging packs 10, 110, 310 disclosed in the remaining figures without affecting operation of the resulting heat exchanging pack.

The heat exchanging packs 10, 110, 210, 310 shown and described herein provide numerous advantages over the heat exchanging packs of the prior art. First, the presence of the one-way valve 45 providing selective and one-way fluid communication between the ambient environment and the interior 28 of the substance receiving portion 11 allows for excessive air to be removed from the substance receiving portion 11 while the mouth 16 is closed and hermetically sealed. The removal of the excess air in turn ensures that the cold or hot substance is maintained in a desired configuration within the substance receiving portion 11 for properly exchanging heat with the portion of the user through the walls 12, 14. Second, the manner in which the strap 80 extends through each of the first passageway 61 and the second passageway 62 allows for at least two loops of the strap 80 to be selectively constricted around the portion of the user without requiring the manipulation of multiple independent components and coupling features. Specifically, the ability to tighten one loop adjacent the mouth 16 of the heat exchanging pack 10, 110, 210, 310 while simultaneously tightening the loop formed by the second portion 102 of the strap 80 substantially simplifies the method of coupling the heat exchanging pack 10, 110, 210, 310 to the portion of the user. Third, the use of a resealable mechanism 33 utilizing a slider mechanism 50 for opening and closing the mouth 16 further simplifies the use of the heat exchanging pack 10, 110, 210, 310 because the slider mechanism 50 can be easily manipulated with only a single hand of the user or a trainer aiding in applying the heat exchanging pack 10, 110, 210, 310. Fourth, the presence of laterally disposed passageways 61, 62 pivotable about first and second partitioning seams 31, 32 allows for a portion of the heat exchanging pack 10, 110, 210, 310 to extend at least partially around the portion of the user to aid in securing the heat exchanging pack 10, 110, 210, 310 to the user. Lastly, the use of any of the releasable coupling methods disclosed herein allows for each of the heat exchanging packs 10, 110, 210, 310 to be used multiple times before disposal thereof, in contrast to the use of traditional heat exchanging packs which typically are discarded after only a single use. The aforementioned advantages in turn lead to a preferable heat exchanging relationship between the cold or hot substance and the portion of the user in need of treatment while securely affixing the position of the heat exchanging pack 10, 110, 210, 310 relative to the portion of the user, thereby eliminating the need for the user to continually apply pressure to the heat exchanging pack to maintain its desired position for exchanging heat.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A heat exchanging pack for treating a portion of a user, the heat exchanging pack comprising:
   a substance receiving portion configured to receive a cold or hot substance therein;
   a first strap receiving portion disposed adjacent a first side of the substance receiving portion, the substance receiving portion having a coupling surface formed on an exterior surface thereof;
   a second strap receiving portion disposed adjacent a second side of the substance receiving portion; and
   a strap configured for releasably coupling the heat exchanging pack to the portion of the body, the strap including a first portion extending through the first strap receiving portion, a second portion extending between the first strap receiving portion and the second strap receiving portion, a third portion extending through the second strap receiving portion, and a fourth portion extending out from the first passageway, wherein the fourth portion releasably attaches to the substance receiving portion.

2. The heat exchanging pack of claim 1, wherein the substance receiving portion includes a one-way valve configured to allow air to pass in a direction from an interior of the substance receiving portion to an ambient environment.

3. The heat exchanging pack of claim 1, wherein the substance receiving portion includes a mouth having a resealable mechanism for selectively opening or closing the mouth, wherein the mouth extends between the first strap receiving portion and the second strap receiving portion.

4. The heat exchanging pack of claim 3, wherein the resealable mechanism includes a slider mechanism configured to open or close the mouth depending on a position of the slider mechanism relative to the mouth.

5. The heat exchanging pack of claim 1, wherein the substance receiving portion is formed between a central portion of a first wall and a central portion of a second wall, wherein the first strap receiving portion is formed between a first lateral portion of the first wall and a first lateral portion of the second wall, and wherein the second strap receiving portion is formed between a second lateral portion of the first wall and a second lateral portion of the second wall.

6. The heat exchanging pack of claim 5, wherein a first partitioning seam joins the first wall to the second wall between the substance receiving portion and the first strap receiving portion and wherein a second partitioning seam joins the first wall to the second wall between the substance receiving portion and the second strap receiving portion.

7. The heat exchanging pack of claim 6, wherein the first partitioning seam and the second partitioning seam are formed during a heat sealing process applied to the first wall and the second wall.

8. The heat exchanging pack of claim 5, wherein the first wall and the second wall are formed from a film of a polymeric material.

9. The heat exchanging pack of claim 8, wherein the polymeric material is one of low-density polyethylene (LDPE), linear low-density polyethylene (LLDPE), or high-density polyethylene (HDPE).

10. The heat exchanging pack of claim 5, wherein the first wall and the second wall are formed from a sheet of material having a fold separating the first wall from the second wall.

11. The heat exchanging pack of claim 1, wherein the substance receiving portion and the second portion of the strap cooperate to form a first opening configured to receive the portion of the user therebetween, and wherein the substance receiving portion and the fourth portion of the strap cooperate to form a second opening configured to receive the portion of the user therebetween.

12. The heat exchanging pack of claim 1, wherein the coupling surface has one of a hook pattern or a loop pattern disposed thereon, and wherein a coupling device disposed on the fourth portion of the strap includes the other of the hook pattern or the loop pattern thereon, the coupling device configured to be releasably coupled to the coupling surface.

13. A method of manufacturing a heat exchanging pack comprising the steps of:
  providing a bag, the bag including a first wall coupled to a second wall at a first side edge and an opposing second side edge of the bag, the bag including a first end edge and an opposing second end edge, the first end edge and the second end edge extending between the first side edge and the second side edge, wherein a mouth is formed adjacent the first end edge;
  forming a first partitioning seam adjacent the first side edge, the first partitioning seam including a first portion of the first wall coupled to a first portion of the second wall, a first passageway formed between the first side edge and the first partitioning seam;
  forming a second partitioning seam adjacent the second side edge, the second partitioning seam including a second portion of the first wall coupled to a second portion of the second wall, a second passageway formed between the second side edge and the second partitioning seam; and
  inserting a continuous strap having a first end and an opposing second end through the first passageway in a direction from the first end edge to the second end edge, extending the strap from the first passageway to the second passageway so the strap extending from the first passageway to the second passages way is disposed exterior and adjacent to the second end edge, and extending the strap through the second passageway in a direction from the second end edge to the first end edge.

14. The method of claim 13, wherein the first partitioning seam and the second partitioning seam are formed in a heat sealing process.

15. The method of claim 13, further comprising the steps of:
  forming an opening at each end of each of the first passageway and the second passageway.

16. A method of using a heat exchanging pack, the method comprising the steps of:
  providing a heat exchanging pack comprising a substance receiving portion configured to receive a cold or hot substance therein, a first strap receiving portion disposed adjacent a first side of the substance receiving portion, a second strap receiving portion disposed adjacent a second side of the substance receiving portion, and a strap configured for releasably coupling the heat exchanging pack to the portion of the body, the strap including a first portion extending through the first strap receiving portion, a second portion extending between the first strap receiving portion and the second strap receiving portion, a third portion extending through the second strap receiving portion, and a fourth portion extending out of the first strap receiving portion;
  placing a portion of a user between the substance receiving portion of the heat exchanging pack and the second portion of the strap;
  extending the fourth portion of the strap out of the first strap receiving portion to constrict the second portion of the strap around the portion of the user.

17. The method of claim 16, further comprising a step of removing air from the interior of the heat exchanging pack through a one-way valve coupled to the substance receiving portion.

18. The method of claim 16, further comprising the steps of:
  extending the fourth portion of the strap around the portion of the user; and
  coupling a coupling device of the fourth portion of the strap to a coupling surface of the substance receiving portion.

* * * * *